(12) United States Patent
Reynaud et al.

(10) Patent No.: US 12,318,468 B2
(45) Date of Patent: Jun. 3, 2025

(54) CHEMICAL COMPOSITION

(71) Applicant: GIVAUDAN SA, Vernier (CH)

(72) Inventors: Romain Reynaud, Reims (FR); Emilie Chapuis, Courcelles (FR)

(73) Assignee: Givaudan SA, Vernier (CH)

( * ) Notice: Subject to any disclaimer, the term of this patent is extended or adjusted under 35 U.S.C. 154(b) by 972 days.

(21) Appl. No.: 16/486,682

(22) PCT Filed: Mar. 7, 2018

(86) PCT No.: PCT/EP2018/055684
§ 371 (c)(1),
(2) Date: Aug. 16, 2019

(87) PCT Pub. No.: WO2018/162604
PCT Pub. Date: Sep. 13, 2018

(65) Prior Publication Data
US 2020/0230046 A1    Jul. 23, 2020

(30) Foreign Application Priority Data

Mar. 8, 2017 (GB) ..................... 1703674

(51) Int. Cl.
| A61K 8/73 | (2006.01) |
| A61K 8/34 | (2006.01) |
| A61Q 5/00 | (2006.01) |
| A61Q 5/12 | (2006.01) |

(52) U.S. Cl.
CPC .............. *A61K 8/735* (2013.01); *A61K 8/347* (2013.01); *A61Q 5/12* (2013.01)

(58) Field of Classification Search
CPC .. A61K 8/735; A61K 8/347; A61K 2800/594; A61K 8/73; A61Q 5/12; A61Q 5/00; A61Q 5/02; A61Q 5/06
See application file for complete search history.

(56) References Cited

U.S. PATENT DOCUMENTS

| 5,023,175 A * | 6/1991 | Hosoya | A61Q 19/00 435/253.4 |
| 6,440,432 B1 * | 8/2002 | Mukherjee | A61Q 17/00 514/59 |
| 2003/0211952 A1 * | 11/2003 | Erazo-Majewicz | A61Q 5/02 510/124 |
| 2011/0003769 A1 * | 1/2011 | Kim | A61K 8/735 514/54 |
| 2012/0171132 A1 | 7/2012 | Bui et al. | |
| 2016/0158128 A1 | 6/2016 | Marsh et al. | |

FOREIGN PATENT DOCUMENTS

| CN | 102085167 A | 6/2011 |
| CN | 106420398 A | 2/2017 |
| EP | 1992645 A1 | 11/2008 |
| JP | 59110612 A | 6/1984 |
| JP | 2003012475 A | 1/2003 |
| JP | 2007297460 A | 11/2007 |
| JP | 2011513481 | 4/2011 |
| JP | 2015512884 B2 | 4/2015 |
| JP | 2016013984 A | 1/2016 |
| RU | 2587014 | 6/2016 |
| WO | 2008000260 A1 | 1/2008 |
| WO | 2009113820 A1 | 9/2009 |
| WO | 2012025615 A2 | 3/2012 |
| WO | 2012089797 A2 | 7/2012 |
| WO | WO 2015069823 * | 5/2015 |

OTHER PUBLICATIONS

International Search Report and Written Opinion of the International Searching Authority for corresponding application PCT/EP2018/055684 dated Jul. 4, 2018.
GB Search Report for corresponding application GB 1703674.0 dated Nov. 29, 2017.
RU Search report in related application RU 2019127914/04 dated Mar. 7, 2018.
Translation of RU Search Report in related application RU 2019127914/04 dated Mar. 7, 2018. related to document 'Sutyagin V.M. et al., "Chemistry and Physics of polymers: Textbook". Tomsk: TPU Publishing, 2003.

* cited by examiner

*Primary Examiner* — Mina Haghighatian

(74) *Attorney, Agent, or Firm* — Norris McLaughlin, P.A.

(57) ABSTRACT

An anti-frizz hair care composition, comprising a low molecular weight hyaluronic acid fraction and a high molecular weight hyaluronic acid fraction.

15 Claims, 5 Drawing Sheets

CHEMICAL COMPOSITION

This is an application filed under 35 USC 371 based on PCT/EP2018/055684 filed 7, Mar. 2018, which in turn is based on GB 1703674.0 filed 8, Mar. 2017. The present application claims the full priority benefit of these prior applications and herein incorporates by reference the full disclosures of these prior applications.

The present invention relates to a hair care composition, to a consumer product for hair care comprising said composition, to their use for hair treatment, in particular an anti-frizz treatment, and to a method of reducing hair frizz.

Mammalian and in particular human hair generally consists of three major components: The cuticle (the outer protective layer), the cortex (the massive core of the hair), and the medulla (a central soft protein core which is more common in thicker hair and particularly so in white hair). The main constituents of these structures are sulfur-rich proteins, lipids, water, melanin, and trace elements.

The cuticle is composed of keratins and usually consists of six to eight layers of flattened overlapping cells. Each cell contains several layers. The uppermost structure of each cuticle cell contains a thin proteinaceous membrane, the epicuticle or f-layer, that is covered with a lipid layer. This layer lipid is covalently attached to the surface of the fibre. The epicuticle is hydrophobic. The cuticle's complex structure allows it to slide as the hair swells, and the f-layer imbues a considerable degree of water resistance. It is critical in protecting the hair and rendering it resistant to the influx and outflow of moisture. The normal cuticle has a smooth appearance, allowing light reflection and limiting friction between the hair shafts. It is primarily responsible for the luster and texture of the hair. The cuticle is a chemically resistant region surrounding the cortex in mammalian hair fibres. The cuticle may be damaged by environmental, mechanical, chemical, and heat sources. Chemical removal of the f-layer, particularly by oxidation during bleaching or perming, eliminates the first hydrophobic defense and leaves the hair more porous and vulnerable. If the cuticle is damaged there is little change in the tensile properties of hair; however, its protective function is diminished.

The cortex contributes almost all the mechanical properties of the hair, particularly strength and elasticity. The cortex consists of closely packed, spindle-shaped cells rich in keratin filaments comprising 400-500 amino acid residues paired together to form proto-filaments which make up a keratin chain. These are orientated parallel to the long axis of the hair shaft and embedded in an amorphous matrix of high sulfur proteins. The keratin chains have a large number of sulfur-containing cystine bonds, which create a strong cross link between adjacent chains. These so-called disulfide bonds are critical in conferring confer shape, stability, and resilience to the hair shaft, and can only be broken by external oxidative chemical agents, such as those used for perming or relaxing. Weak hydrogen bonds link the keratin polypeptide chains together. These weaker bonds are easily overcome by water, rendering curly hair temporarily straight. The powerful disulfide bonds and weaker hydrogen bonds are crucial to hair health. The cortex also contains melanin granules, which are responsible for the color the fibre.

The medulla is a soft proteinaceous core present in thicker and white hair. It has no known function in humans.

Hair care compositions have been used for many decades and for many different uses. For example, there are hair cleansing compositions, hair conditioning compositions, and hair styling compositions. Many of these compositions that are known are water-based formulations.

Hair cleansing compositions are generally effective to remove soil from hair. The soil includes natural exudations from the scalp, environmental agents, and styling products. The soil can coat or deposit on the hair and scalp. Hair coated with such soil is typically greasy in feel and appearance, heavy to the touch, possibly malodorous, and generally unable to maintain a desired style. Known cleansing compositions typically include a combination of water and surface-active ingredients, such as soap or synthetic surfactants, and may also include a non-aqueous blend of starches. The combination of water and surface-active agents emulsifies the soil from the hair and scalp, allowing it to be rinsed away.

Cleansing compositions may also contain conditioning agents that deposit on the hair and scalp during rinsing with water. Such conditioning agents can include polymers, oils, waxes, protein hydrolysates, silicones, and mixtures and derivatives thereof. In addition, the conditioning composition can be a separate and different product from the cleansing composition.

Conditioning compositions that are known in the art are typically water-based formulations. However, there are also known conditioning compositions, which include at least one of silicones; animal, mineral or vegetable oils; waxes; petrolatums; and greases. The water-based conditioning compositions typically include substituted cationic waxes, fatty alcohols, cationic polymers, hydrolysed proteins and derivatives thereof, and fragrances. Such conditioning formulations impart combabilty and manageability to the treated hair, thereby minimizing breakage during the styling process and resulting in shiny, healthy, and manageable hair. Conditioning compositions may also be effective to moisturize the hair. Subsequent drying and styling processes can include air drying or heating.

Hair is often subjected to a wide variety of insults that can cause damage. These include shampooing, rinsing, drying, heating, combing, styling, perming, coloring, exposure to the elements, etc. Thus, hair is often in dry, rough, lusterless or frizzy due to abrasion of the hair surface and removal of the hair's natural oils and other natural conditioning and moisturizing components. Additionally, hair is subjected to weather-related changes, such as changes in humidity, which can leave hair in a frizzy condition.

In particular, curly hair tends to become frizzy and significantly expand in volume when exposed to high humidity conditions or changes in the ambient humidity level. These changes in shape and body of the hair are believed to result from increased water uptake into the hair follicle.

Hair frizz can take a number of different forms. It can occur when fibres, which can be visually seen, depart from the bulk or fall out of alignment of a desired hair style pattern. Frizz occurs due to environmental changes, such as humidity fluctuations and static electricity build-up, and as a result of a person's daily normal motion and activities that may cause hair fibres to shift and interlock.

Hair fibre alignment can also impact the shiny appearance of the hair. Hair fibres that are aligned parallel to each other show a minimum scattering of light as well as increased specular light reflection. A material that can adhere well to hair fibres, creating a bridge between neighboring fibres, results in such an alignment, thus improving the appearance of shiny hair.

Frizz often causes expanded and unruly hair and makes it difficult to control the hair style. For consumer who desire well aligned hair, such expanded and unruly hair is not desirable. The term "frizz control" as used herein means to control hair frizz, i.e. to reduce frizz of the hair or to prevent hair from becoming frizzy.

A variety of approaches has been developed to alleviate hair frizz. These include heat treatment for temporary straightening, reactive chemistry approaches aimed at a permanent restructuring of hair, and application of oily leave-on products to weigh down hair.

The use of heated instruments allows the potential for molecular rearrangement within the hair shaft. The keratinaceous structure of hair fibrils relies on bonding to create the characteristic structure of the hair. The bonds within the keratin fibre include cysteine bonds, salt bonds, and hydrogen bonds. The salt and hydrogen bonds are influenced by the presence of water within the hair. These bonds are much weaker than the cysteine bonds and allow movement within the keratin structure to occur and allow for hair frizz due to exposure to high humidity conditions. It is known that frizz can be temporarily abated by the use of hot implements, such as blow dryers, in combination with styling under tension, e.g., pulling with a brush or comb, or with tension styling in combination with flat or round heated irons. The presence of moisture and the influence of heat and tension allow the rearrangement of the weak salt and hydrogen bonds and creates a straight, although temporary, restyling of the hair. Unless some means of maintenance of the new style is present during the restyling process, reversion to the original configuration of the hair typically ensues.

The use of reactive chemistry provides a permanent frizz reduction benefit. However, the reactive chemistry methods and compositions are harsh on the hair structure and can cause hair to split or break and can also result in a loss of hair shine. Skin and/or eye irritation from the relatively harsh chemicals used in reactive chemistry methods is also common.

Typically, leave-on conditioner type hair care formulations provide advantages over the more permanent frizz reduction approaches. For example, leave-on formulations are typically less damaging to the hair. Also, leave-on formulations are more convenient because the consumer can use the product at any time and then wash the product out of the hair with one washing. Another benefit is that the product may be applied to those parts of the hair most in need of the frizz control benefits.

The use of polymeric materials can prevent the immediate reversion from a straight conformation to hair's original configuration. There are known polymeric formulations, e.g., fixative polymers, which coat the surface of the hair with a cement- or glue-like layer that externally restricts the movement of the hair and reinforces the straight conformation. Polyvinyl pyrrolidone and derivatives thereof, or acrylic acid-based polymers and derivatives thereof, have been widely used as fixative polymers. These polymeric compositions are formulated to resist humidity but do not provide a sufficiently hydrophobic barrier to water absorption to prevent the onset of frizz.

Commonly, hair conditioning benefits are provided through the use of hair conditioning agents such as cationic surfactants, cationic polymers, silicone conditioning agents, hydrocarbon and other organic oils, and solid aliphatics, such as fatty alcohols. These conditioning agents are well known in the art (see, for example, WO 97/35542, WO 97/35545, or WO 97/35546, all of which describe the use of conditioning agents in shampoo compositions). However, such conditioning agents are often impractical for use in the large quantities necessary to reduce hair frizz. Usage of large amounts of conditioning agents that work to control hair frizz by coating and weighing down the hair commonly results in a poor perception of hair cleanliness and hair feel, for example, leaving the hair and hands with a tacky, dirty feeling.

Hydrophobing agents, such as silicones, for example, dimethicones and cyclomethicones, or fluorine-based polymers are known to provide a hydrophobic barrier on the surface of the hair. Due to their molecular characteristics, hydrophobing agents also afford shine, lubricity, and water resistance to the hair. However, silicones and fluoropolymers are typically oily in nature and difficult to remove, which can contribute to build-up on the hair. In addition, silicones have been recognized for potential toxicity and negative impacts on the environment.

Several different anti-frizz agents have been described in the prior art:

WO 01/91707 and US 2001/0043912 both describe hair care compositions comprising selected dimethicone copolyol frizz control agents, and/or selected PEG modified frizz control agents, in combination with a polysiloxane resin, a lipid vehicle material, and a cationic surfactant vehicle material for frizz control while retaining good conditioning, shine, hair feel, and appearance.

US 2002/0197227 describes hair care compositions that provide frizz control an maintain volume for naturally curly hair in high humidity environments. These compositions comprise a high viscosity flexible polydimethylsiloxane polymer and a mixture of volatile and non-volatile carrier fluids.

US 2011/0265810 relates to a hair care compositions, which includes a volatile hydrocarbon-containing component; a non-volatile hydrocarbon-containing component; and an oil-soluble polymer component. Said composition is used for forming a hydrophobic barrier on hair to render the hair substantially resistant to moisture absorption.

WO 2015/035164 describes hair care and styling compositions for providing shine, frizz control, and temporary styling benefits. Said hair treatment compositions comprise viscoelastic particles in an aqueous carrier or a mixture of water with an organic or silicone carrier.

However, most commercially available compositions claiming anti-frizz benefits do not perform at a satisfactory level and consumers complain about the trade-off between long-lasting performance, feel, and appearance they have to navigate through to achieve their desired look.

It is therefore a problem of the present invention to provide an improved hair care composition that provides an anti-frizz effect and at the same time keeps the hair shiny and well moisturized.

Figure 7:
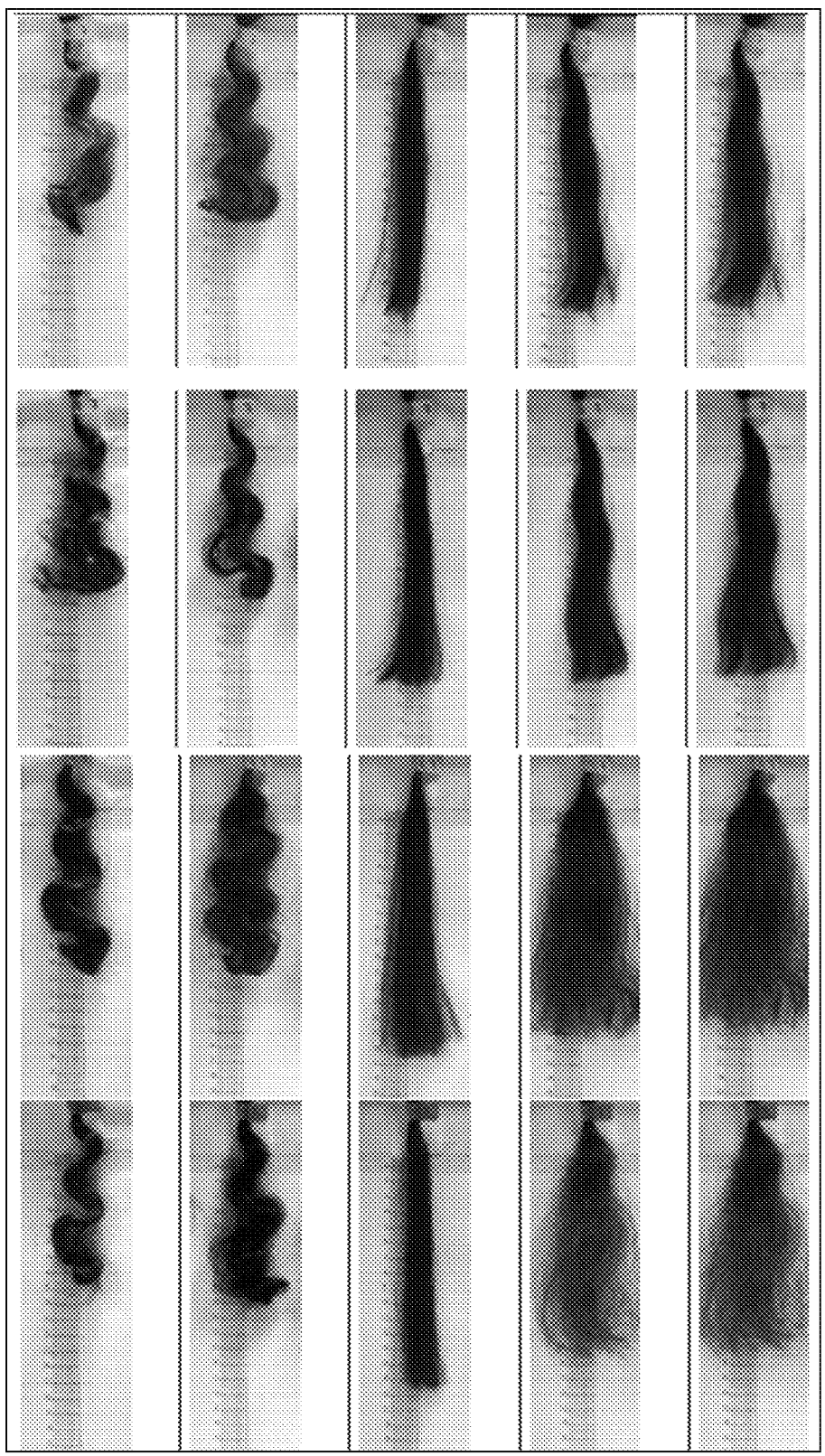

FIG. 7 provide photographs taken for treatments with water, placebo shampoo and shampoos according to the invention.

Figure 8:
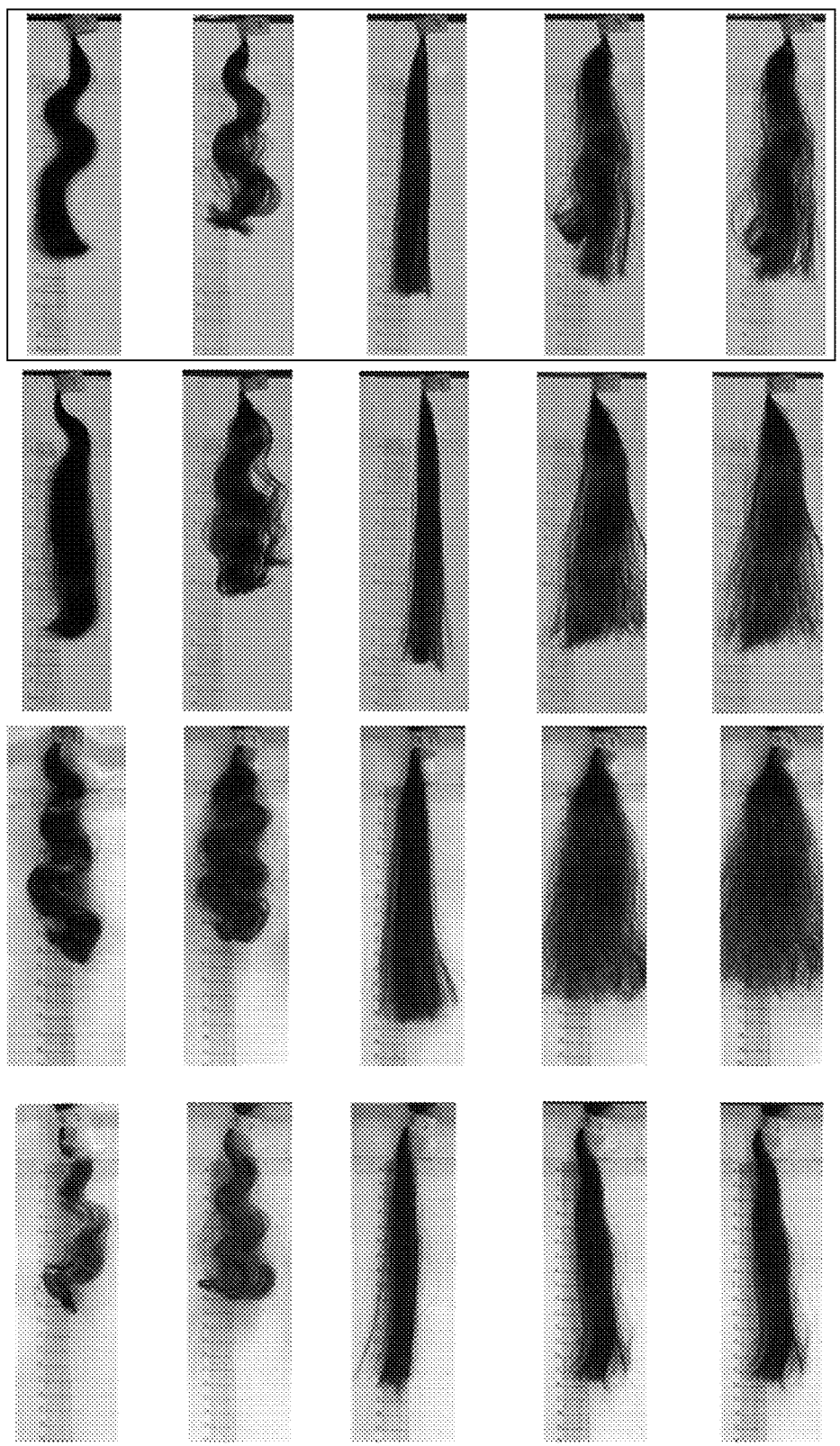

FIG. 8 provide photographs taken for treatments with water, placebo shampoo and shampoos according to the invention.

Figure 9:
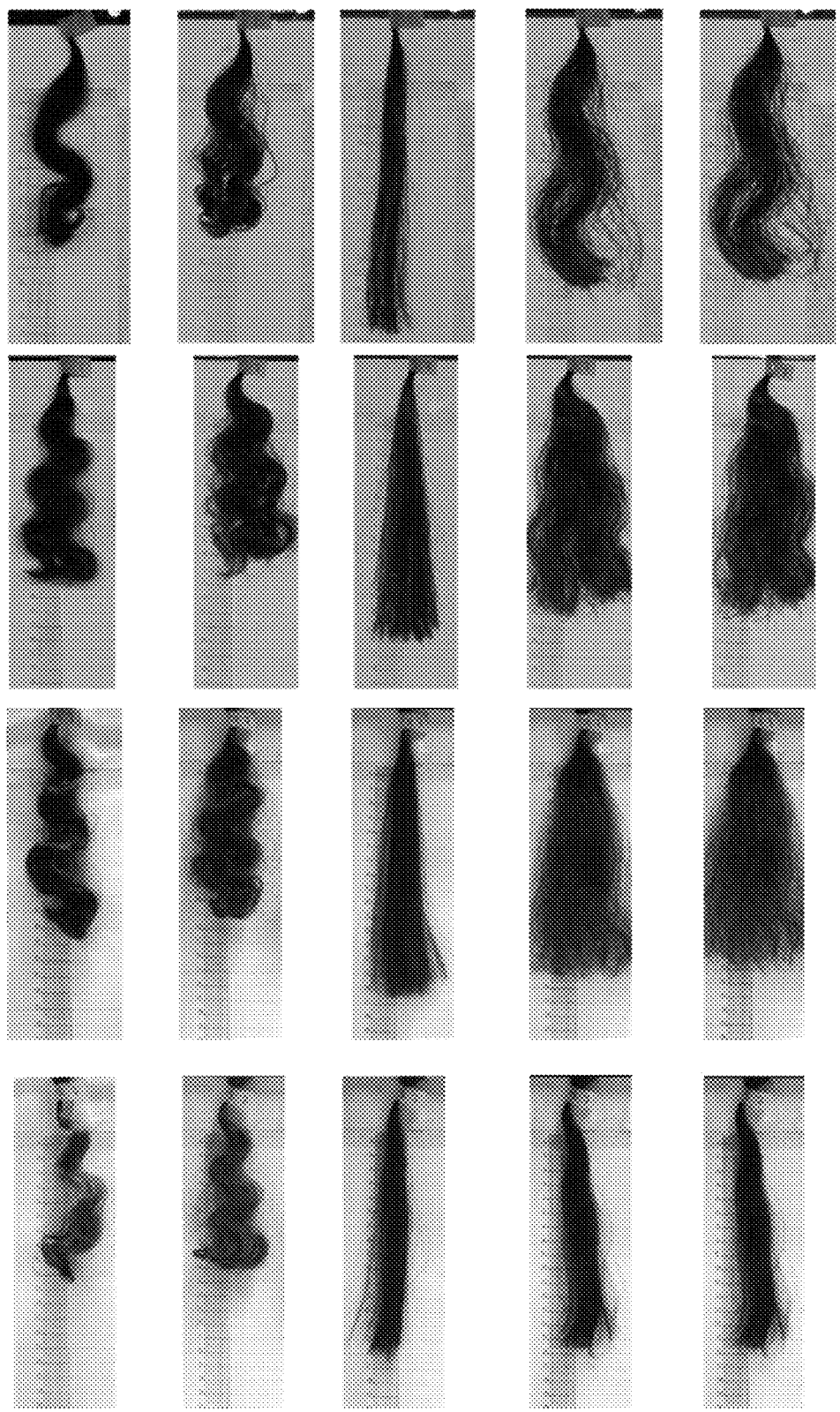

FIG. 9 provide photographs taken for treatments with water, placebo shampoo and shampoos according to the invention.

This problem is solved by the hair care composition according to claim 1, the consumer product for hair care according to claim 8, their use for hair treatment according to claim 12, and the method of reducing hair frizz according to claim 13. Preferred embodiments are the subject of the dependent claims.

In a first aspect, the present invention provides a hair care composition, comprising a low molecular weight hyaluronic acid fraction and a high molecular weight hyaluronic acid fraction. Said low molecular weight hyaluronic acid fraction comprises hyaluronic acid or a salt or derivative thereof having a weight-average molecular weight $M_w$ of less than 50 kDa. Said high molecular weight hyaluronic acid fraction comprises hyaluronic acid or a salt or derivative thereof having a weight-average molecular weight $M_w$ of more than 1 MDa.

The weight-average molecular weight $M_w$ is calculated with SEC-MALLS (Size Exclusion Chromatography combined with Multi-Angle Laser Light Scattering) or by converting the intrinsic viscosity into molecular weight thanks to the Mark Houwink equation.

Both the low molecular weight hyaluronic acid fraction and the high molecular weight hyaluronic acid fraction preferably have a dispersity $Đ_m$ of between 1 and 2, with $Đ_m$ being defined by the equation $Đ_m = M_w/M_n$, where $M_w$ is the weight-average molecular weight and $M_n$ is the number-average molecular weight.

In a second aspect, the present invention provides a consumer product for hair care, comprising the hair care composition according to the present invention.

In a third aspect, the present invention refers to the use of said hair care composition or consumer product for hair treatment.

In a fourth aspect, the present invention provides a method of reducing hair frizz by applying to the hair an effective amount of the hair care composition or of the consumer product according to the present invention.

Surprisingly, it was found that application of the hair care composition of the present invention to a hair fibre leads to a coating of the hair surface. More precisely, as revealed by hair fibre ultrastructural analysis, the hyaluronic acid covers the epicuticle lipid layer. This cover protects the cuticle from lifting due to mechanical stress (as seen in example 5 below). Thereby, hair shininess is improved, and hair breakage and hair tangling is decreased.

In particular, as has been shown by in vitro studies on hair strands with different curly levels (see example 7), the composition of the present invention has a significant anti-frizz effect and keeps the hair straight for much longer, even under high moisture conditions.

Furthermore, the epicuticle lipid layer, i.e. the f layer, is protected. This layer is critical in protecting the hair and regulating the influx and outflow of moisture. Thus, the hair care composition of the present invention acts as a water transit shield.

Overall, the hair care composition of the present invention improves the beauty of the hair and makes the hair feel healthy.

The hair care composition of the present invention comprises both a low molecular weight hyaluronic acid fraction and a high molecular weight hyaluronic acid fraction.

"Hair", as used herein, means mammalian hair including scalp hair, facial hair, and body hair, particularly hair on the human head and scalp.

"Hyaluronic acid", as used herein, is meant to include hyaluronic acid itself, as well as salts or derivatives thereof, if not noted otherwise. The abbreviation "HA" is used interchangeably.

"Derivatives", as used herein, includes but is not limited to, amide, ether, ester, amino, carboxyl, acetyl, acid, and/or alcohol derivatives of a given compound.

"Polymer", as used herein, means a chemical formed from the polymerisation of two or more monomers, which may be the same or different. The term "polymer" as used herein shall include all materials made by the polymerisation of monomers, as well as natural polymers. Polymers made from only one type of monomer are called homopolymers. Polymers made from two or more different types of monomers are called copolymers. The distribution of the different monomers can be statistical or block-wise. Except if stated otherwise, the term "polymer" used herein includes any type of polymer including homopolymers and copolymers.

The term "consumer product for hair care" includes both leave-on products and wash-out, such as shampoos, sprays, lotions, etc. More detailed examples are given below.

"Cosmetically acceptable", as used herein, means that the compositions, formulations or components described are suitable for use in contact with human keratinous tissue without undue toxicity, incompatibility, instability, allergic response, and the like. All compositions described herein, which have the purpose of being directly applied to keratinous tissue, are limited to those being cosmetically acceptable.

If not indicated otherwise, concentrations given in "%" refer to "% by weight" throughout this application.

The effects of the hair care compositions and the consumer products of the present invention were studied in several in vitro and in vivo studies (see examples below). Some of these studies involved the application of thermomechanical stress or high humidity to the hair. It was found that the hair care compositions and consumer products of the present invention improved hair shininess (+9.6%) and strength of the hair fibre, reduced brittle hair (−65%) and cuticle lifting, and also significantly improved hydration and aspect (more volume with less frizz). In the in vivo studies, it was demonstrated that the hair care compositions and the consumer products of the present invention provided the hair with more volume and softness, and a more homogenous look.

Overall, it was found that the hair care compositions and the consumer products of the present invention render the hair more beautiful by increasing its shininess, hydration, strength, volume, softness, and avoiding the flat aspect. In particular, the compositions and products provide natural volume enhancement, anti-frizz protection, mechanical and thermal protection, straightening, hair resistance increase, hair shininess boost, biological hair hydration, and hair softness enhancement.

The low molecular weight hyaluronic acid fraction of the hair care composition of the present invention comprises hyaluronic acid or a salt or derivative thereof having a weight-average molecular weight $M_w$ of less than 50 kDa.

In a preferred embodiment, the low molecular weight hyaluronic acid fraction comprises hyaluronic acid or a salt or derivative thereof having a weight-average molecular weight $M_w$ of 1 to 50 kDa, preferably 10 to 50 kDa, most preferably of 20 to 50 kDa.

The high molecular weight hyaluronic acid fraction of the hair care composition of the present invention comprises hyaluronic acid or a salt or derivative thereof having a weight-average molecular weight 114, of more than 1 MDa, preferably with a dispersity $Đ_m$ of between 1 and 2.

In a preferred embodiment, the high molecular weight hyaluronic acid fraction comprises hyaluronic acid or a salt or derivative thereof having a weight-average molecular weight $M_n$ of 1 to 20 MDa, preferably 1 to 5 MDa, most preferably of 1 to 2 MDa.

In a preferred embodiment, the hair care composition of the present invention comprises no or essentially no hyaluronic acid or a salt or derivative thereof of intermediate molecular weight, having a weight-average molecular weight of more than 50 kDa to less than 1 MDa.

The hair care composition of the present invention may be employed for hair treatment as such or may be diluted prior to use. Preferably, the hair care composition of the present invention is a concentrate intended to be diluted and/or mixed with other active ingredients to form a consumer product prior to use.

In a preferred embodiment, the hair care composition of the present invention comprises at least 0.1% by weight of the low molecular weight hyaluronic acid fraction, preferably 1% to 10% by weight, more preferably 2% to 5% by weight, and most preferably 2.5% to 3% by weight. Such a composition is typically diluted and/or mixed with other active ingredients to form a consumer product prior to use.

In a preferred embodiment, the hair care composition of the present invention comprises at least 0.1% by weight of the high molecular weight hyaluronic acid fraction, preferably 0.1% to 5% by weight, more preferably 0.2% to 2% by weight, and most preferably 0.5% to 1% by weight. Such a composition is typically diluted and/or mixed with other active ingredients to form a consumer product prior to use.

In a preferred embodiment, the weight ratio of the low molecular weight hyaluronic acid fraction to the high molecular weight hyaluronic acid fraction is 1:1 to 10:1, preferably 2:1 to 6:1, more preferably 3:1 to 5:1.

In a preferred embodiment, the hair care composition of the present invention comprises about 2% to 5% of a hyaluronic acid mixture, up to about 2% of 80% lactic acid, and up to about 3% of phenoxyethanol, wherein the hyaluronic acid mixture comprises about 0.6% to 0.9% of high molecular weight hyaluronic acid and about 2.4% to about 2.7% of low molecular weight hyaluronic acid. In a particularly preferred embodiment, it comprises about 3.3% of the hyaluronic acid mixture, about 1% of 80% lactic acid, and about 1.2% of phenoxyethanol. The remainder is preferably pure water, but may also contain suitable additives and/or solvents.

In a preferred embodiment, the hair care composition of the present invention further comprises a cationic conditioner, in particular hydroxypropyl guar hydroxypropyl trimonium chloride. This improves the adherence to the hair.

It is also possible to use a suitable other cationic conditioner. Preferably, the hair care composition of the present invention comprises about 0.01 to about 0.5% by weight of hydroxypropyl guar hydroxypropyl trimonium chloride.

Alternatively, hydroxypropyl guar hydroxypropyl trimonium chloride or a suitable other cationic conditioner may be added to the hair care composition or consumer product of the present invention prior to use.

Consequently, in another aspect, the present invention also provides a method of improving the adherence of hyaluronic acid to the hair, wherein a cationic conditioner is added to a hair care composition or consumer product containing said hyaluronic acid, and in particular to the hair care composition or consumer product of the present invention. Preferably, hydroxypropyl guar hydroxypropyl trimonium chloride is added.

As a particularly preferred example, the composition of the present invention may contain, e.g., 2.4 to 2.7% of the low molecular weight hyaluronic acid fraction, 0.6 to 0.8% of the high molecular weight hyaluronic acid fraction, 0.8% of lactic acid (neat), and water (qsp 100). More preferably, the composition contains 2.4 to 2.7% of the low molecular weight hyaluronic acid fraction, 0.6 to 0.8% of the high molecular weight hyaluronic acid fraction, 0.8% of lactic acid (neat), 1.2% of phenoxyethanol, and water (qsp 100).

Most preferably, a consumer product ready for use will contain about 1.5 to 3% of such a hair care composition.

The present invention further provides a consumer product for hair care comprising said hair care composition.

Preferably, the consumer product comprises at least 1% by weight of the hair care composition according to the present invention, preferably 1% to 5% by weight, and most preferably 1.5% to 3.5% by weight.

The consumer product of the present invention may be any product typically used for hair care, including but not limited to a shampoo, conditioner, spray, treatment, mask, strengthener, pre-shampoo, lotion, serum, cream, foam, mousse, and gel. Particularly preferably, the consumer product is a shampoo, anti-frizz hair spray, beauty hair mask, hair shininess serum, hair conditioner, hair strengthener pre-shampoo, or hair protection lotion.

The consumer product according to the present invention may further comprise one or more materials selected from the group consisting of carriers, solvents, surfactants, thickeners, styling polymers, anti-dandruff actives, antimicrobial materials, skin and scalp actives, vitamins, salts, buffers, hair growth agents, conditioning materials, hair-fixative polymers, fragrances, colorings/colorants, dyes, pigments, opacifiers, pearlescent aids, oils, waxes, preservatives, sensates, sunscreens, medicinal agents, antifoaming agents, antioxidants, binders, biological additives, buffering agents, bulking agents, chelating agents, chemical additives, film formers or materials, pH adjusters, propellants, oxidizing agents, and reducing agents.

All additives should be physically and chemically compatible with the essential components of the hair care composition or consumer product, and should not otherwise unduly impair stability, aesthetics or performance. Most importantly, they should also be cosmetically acceptable.

Hair care products typically comprise a carrier, which is present at a level from about 20 wt % to about 99 wt %. The carrier may comprise water, organic solvents (miscible or non-miscible with water) silicone solvents, and/or mixtures thereof. The solvents should be dermatologically acceptable. Carriers usually do not comprises more than about 2 wt % of non-volatile solvent, as significantly higher concentrations will increase hair weigh-down and greasy feel. Water, organic and silicone solvents that have boiling points below or equal to 250° C. are considered volatile solvents. Suitable carriers typically include water and water solutions of lower alkyl alcohols, such as monohydric alcohols having 1 to 6 carbons (e.g. ethanol and/or isopropanol), and polyhydric alcohols, such as glycols, glycerine, and other diols.

As thickeners, the hair care composition or consumer product may comprise rheology modifiers to improve feel, in-use properties and suspending stability. For example, rheological properties may be adjusted so that the composition or product remains uniform during its storage and transportation and does not drip undesirably onto other areas of the body, clothing or home furnishings during its use. Any suitable rheology modifier can be used. Typically, about 0.01 to about 3 wt % of thickener is included. Examples of suitable thickeners are disclosed in WO 2015/035164 and US 2001/0043912, the contents of which in this respect are herewith incorporated by reference.

The compositions and products of the present invention can additionally also comprise any suitable optional ingredients as desired. Such optional ingredients should be physically and chemically compatible with the components of the composition or product, and should not otherwise unduly impair stability, aesthetics or performance. The CTFA Cosmetic Ingredient Handbook, Tenth Edition (published by the Cosmetic, Toiletry, and Fragrance Association, Inc., Washington D.C.) (2004) describes a wide variety of non-limiting materials that can be added to the compositions and products of the present invention.

For instance, the composition and product of the present invention can include a styling polymer. A styling polymer may be selected from the group consisting of acrylate polymers and their esters, methacrylate polymers and their esters, acrylate copolymers and their esters, methacrylate copolymers and their esters, polyurethane polymers and copolymers, polyvinylpyrrolidones (PVP), PVT-polyvinyl acetate copolymers, PVP-polyvinyl alcohol copolymers, polyesters, and other polymers.

The hair care compositions and consumer products of the present invention may also comprise a sensate. As used herein, the term "sensate" refers to a substance that, when applied to the skin, causes a perceived sensation of a change in conditions, for example but not limited to heating, cooling, refreshing, and the like. Sensates are preferably utilized at levels from about 0.001 to about 10 wt % of the consumer product. Examples of suitable sensates include camphor, menthol, L-isopulegol, ethyl menthane carboxamide, and trimethyl isopropyl butanamide.

The compositions and consumer products of the present invention may also contain optional components, which modify the physical and performance characteristics. Such components include surfactants, salts, buffers, thickeners, solvents, opacifiers, pearlescent aids, preservatives, fragrances, colorants, dyes, pigments, chelators, sunscreens, vitamins, and medicinal agents. Optional components that are among those useful herein are disclosed in U.S. Pat. No. 4,387,090, the contents of which in this respect are herewith incorporated by reference.

The compositions and consumer products of the present invention may also optionally contain an anti-dandruff agent for providing anti-microbial activity. The anti-dandruff agent may be particulate or soluble. Preferred anti-dandruff agents include, but are not limited to, particulate crystalline anti-dandruff agents, such as sulfur, selenium sulphide, and heavy metal salts of pyridinethione. Especially preferred is zinc pyridinethione. Soluble anti-dandruff agents, such as ketoconazole, are also known in the art. An anti-dandruff agent is preferably present in a concentration of about 0.1 to 4 wt %.

The compositions and consumer products of the present invention may also optionally contain hair growth agents, such as zinc pyridinethione. The compositions and consumer products of the present invention may also optionally contain a compound useful for regulating the growth and loss of hair. Such compounds known in the art include lupine triterpenes and derivatives thereof, derivatives of oleanane triterpenes and ursane triterpenes, and salts and mixtures thereof, minoxidil (6-(1-piperidinyl)-2,4-pyrimidinediamine 3-oxide), or finasteride.

The compositions and consumer products of the present invention may also optionally contain salts and/or buffers in order to modify the rheology. For example, salts, such as potassium chloride and sodium chloride, may be added at levels from about 0.001 to about 1 wt %. Buffers, such as citrate or phosphate buffers, may also be used. Preferably, the pH of the present consumer products are modified to a pH from about 3 to about 10, preferably from about 3 to about 7.

The compositions and consumer products of the present invention may also optionally contain additional conditioning polymers, in particular cationic conditioning polymers. If present, these are preferably employed at a level of from about 0.5 to about 10 wt %. Suitable cationic conditioning polymers are disclosed in US 2001/0043912, for instance, the disclosure of which in this respect is herewith incorporated by reference.

A wide variety of other additional components can be formulated into the present compositions and consumer products. These include: other conditioning agents, such as hydrolysed collagen, vitamin E, panthenol, panthenyl ethyl ether, hydrolysed keratin, proteins, plant extracts, and nutrients; hair-fixative polymers, such as amphoteric, non-ionic, cationic, and anionic fixative polymers, and silicone grafted copolymers; preservatives, such as benzyl alcohol, methyl paraben, propyl paraben, and imidazolidinyl urea; pH adjusting agents, such as glutamic acid, citric acid, sodium citrate, succinic acid, phosphoric acid, lactic acid, sodium hydroxide, and sodium carbonate; salts in general, such as potassium acetate and sodium chloride; coloring agents; hair oxidizing (bleaching) agents, such as hydrogen peroxide, perborate, and persulfate salts; hair reducing agents, such as thioglycolates; fragrances; and sequestering agents, such as disodium ethylenediamine tetra-acetate; ultraviolet and infrared screening and absorbing agents, such as octyl salicylate; and mixtures thereof.

Additional optional ingredients include, but are not limited to: skin and scalp actives, oils, waxes, antifoaming agents, antioxidants, binders, biological additives, bulking agents, chelating agents, chemical additives, film formers or materials, and propellants.

The consumer product of the present invention may in general be of any form typically used for hair care. In particular, it may be in provided as described in WO 2015/035164 under section F. "Composition Form" (pages 17-19), the disclosure of which in this respect is herewith incorporated by reference.

The consumer product of the present invention may be applied to either wet or dry hair, depending on formulation.

The present invention also refers to the use of said hair care composition or consumer product for hair treatment. To this end, the hair care composition or consumer product may be applied to wet or dry hair. Optionally, depending on the formulation, the hair may be rinsed, e.g. with water, after the application.

The present invention further provides a method of reducing hair frizz by applying to the hair an effective amount of the hair care composition or of the consumer product described herein above.

The present invention is further illustrated by means of the following non-limiting examples:

EXAMPLE 1: HAIR CARE COMPOSITION COMPRISING A MIXTURE OF LOW AND HIGH MOLECULAR WEIGHT HYALURONIC ACID

A basic hair care composition was obtained by mixing the following components

| | |
|---|---|
| Low molecular weight hyaluronic acid: | 2.7 wt % |
| High molecular weight hyaluronic acid: | 0.67 wt % |
| Lactic acid (neat): | 0.8 wt % |
| Water: | qs 100% |

EXAMPLE 2: PRODUCTS TESTED IN SHAMPOO FORM

The basic hair care composition from Example 1 was incorporated in a number of products in shampoo form for testing.

The INCI composition of each formulated product is described below:

Shampoo A (Placebo): AQUA/WATER, SODIUM LAURETH SULPHATE, COCAMIDOPROPYLBETAINE, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo B (with 1.5% HA Mixture and Guar): AQUA/WATER, SODIUM LAURETH SULPHATE, COCAMIDOPROPYLBETAINE, 1.5% of the composition from Example 1, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo C (with 3% HA mixture and Guar): AQUA/WATER, SODIUM LAURETH SULPHATE, COCAMIDOPROPYLBETAINE, 3% of the composition from Example 1, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo D (with 3% HA mixture, but without Guar): AQUA/WATER, SODIUM LAURETH SULPHATE, COCAMIDOPROPYLBETAINE, 3% of the composition from Example 1, SODIUM CHLORIDE, PHENOXYTHANOL, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo E (with 3% LMW HA and Guar): AQUA/WATER, SODIUM LAURETH SULPHATE, COCAMIDOPROPYLBETAINE, LOW MOLECULAR WEIGHT HYALURONIC ACID, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo F (with 3% HMW HA and Guar): AQUA/WATER, SODIUM LAURETH SULPHATE, COCAMIDOPROPYLBETAINE, HIGH MOLECULAR WEIGHT SODIUM HYALURONATE, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

Shampoo G (with 0.8% Lactic Acid and 0.2% Guar): AQUA/WATER, SODIUM LAURETH SULPHATE, COCAMIDOPROPYLBETAINE, LACTIC ACID, SODIUM CHLORIDE, PHENOXYTHANOL, HYDROXYPROPYL GUAR HYDROXYPROPYL TRIMONIUM CHLORIDE, FRAGRANCE, CITRIC ACID, SODIUM HYDROXIDE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE.

All shampoos were provided in a jar of 50 ml and stored at ambient temperature away from light. These shampoos were used in the studies described in the further examples.

EXAMPLE 3: PRODUCTS TESTED IN SPRAY FORM

The basic hair care composition from Example 1 was incorporated in a number of products in spray form for testing.

The INCI composition of each formulated product is described below:

Spray A (Placebo): AQUA/WATER, ALCOHOL, PHENOXYTHANOL, FRAGRANCE, BUTYLPHENYL METHYLPROPIONAL, D-LIMONENE, ALPHA-ISOMETHYL IONONE, LINALOOL.

Spray B (with 3% HA): AQUA/WATER, ALCOHOL, 3% of the composition from Example 1, PHENOXYTHANOL, FRAGRANCE, BUTYLPHENYL METHYLPROPIONAL, D-LIMONENE, ALPHA-ISOMETHYL IONONE, LINALOOL, SODIUM HYDROXIDE.

Products were stored at ambient temperature away from light. These hair sprays were used in the studies described in the further examples.

EXAMPLE 4: ASSESSMENT OF PRODUCT DEPOSITION ON HAIR FIBRE BY MICROSCOPY

Three identical strands of human Euro-natural hair (51 cm total length; weight: 120 g; colour: blond) were selected for this study. One strand was left untreated (comparative example), while the other two were treated with shampoo A (comparative example) and with shampoo C, respectively.

The untreated hair strand was washed with water and stained with blue alcian.

The two shampoo treated hair strands were rinsed in 200 ml of water for 15 s, followed by application of 0.5 g of shampoo per 2 g of hair. Once the shampoo was applied, a gentle massage was done before leaving the hair strands for 2 min. The thus treated hair strands were rinsed abundantly three times during 15 s in 200 ml of water each. After that, the hair strands were dried with paper and subsequently a hair dryer during 3 min.

All hair strands were stained with blue alcian. This staining technique was adapted for hair fibre samples without fixation and without paraffin inclusion. Blue alcian is used to stain acidic polysaccharides such as glycosaminoglycans and hyaluronic acid. To this end, a solution of blue alcian at 1% (American masterTech, ref KTABP2.5) was diluted in acetic acid at 3%. The hair strands were stained in this solution for 20 min and then rinsed several times with distilled water.

The three samples were then observed under a light microscope and under a transmission electron microscope.

Under the light microscope, blue alcian staining is strongly visible only in the sample treated with shampoo C. It was thus concluded that the hyaluronic acid contained in shampoo C stayed on the hair fibre surface and formed a kind of film around the hair fibre.

Figure 1:
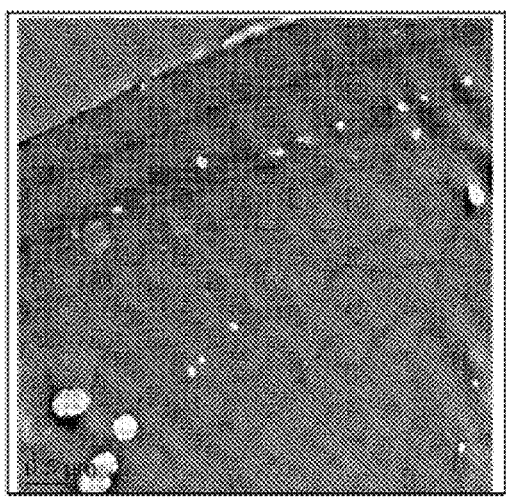
FIG. 1 shows a transmission electron microscope image of untreated hair fibres.
Figure 2:
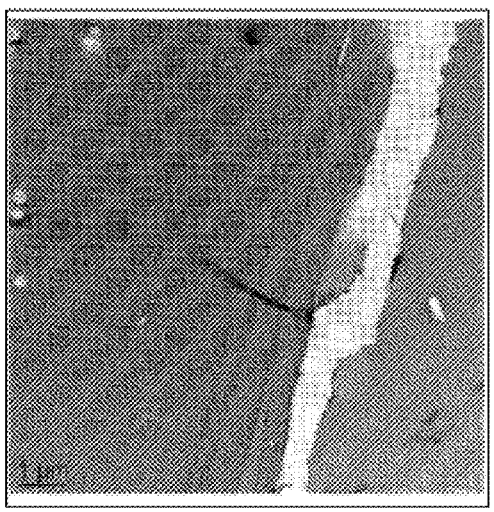
FIG. 2 shows a transmission electron microscope image of hair fibres treated with a shampoo not according to the invention.
Figure 3:
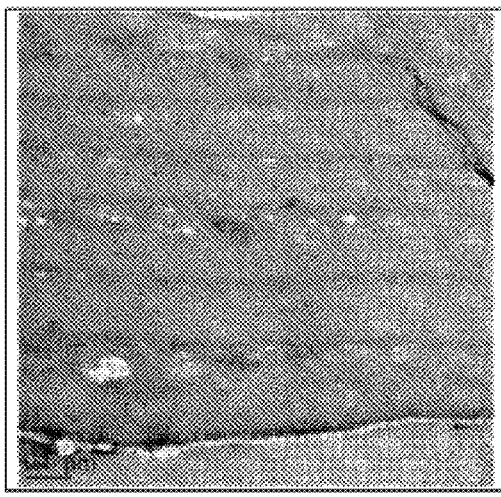
FIG. 3 shows a transmission electron microscope image of hair fibres treated with a shampoo according to the invention.

Using the transmission electron microscope, it was possible to investigate the hair fibres at the ultrastructural level. The results are shown in FIGS. 1 (untreated), 2 (shampoo A), and 3 (shampoo C), respectively.

Interestingly, it was found that the hair treated with shampoo C was more resistant to the sample preparation process. In particular, the cuticle was thicker, having at least 6 layers of flattened cells. In contrast thereto, in the untreated and placebo treated samples, the cuticle was thinner, having only two layers of cells. Also, the cuticle was often broken for the comparative examples.

EXAMPLE 5: SHININESS, BRITTLENESS AND MICROSCOPIC STUDIES 61 identical strands of Euro-natural hair (20 cm of total length, 18 cm of free hair, colour: 6/0) were selected for these studies. One strand was left untreated (comparative example), and 20 hair strands each were treated with shampoo A (comparative example), with shampoo B, or with shampoo C, respectively.

To the wet hair strands, 0.5 ml of shampoo was applied per 2 g of hair. After applying a gentle massage during 1 min, the hair strands were rinsed with water abundantly during 30 s.

Shininess

To assess shininess, non-cross-polarised photographs were used. This technique consists of obtaining high resolution photographs of the hair strands, in reproducible lighting conditions. The acquisitions were carried out with a high resolution camera. The lens used was a Nikkor 60 mm equipped with a filter. Lighting was provided by two flashes. The flash heads were fitted with filter slots to hold polarising gel (HN32 Sarelec, France). In order to obtain the non-cross polarised photographs, the camera filter was switched to 90° relative to its polarised position. The evaluation was carried out in a dark room under monitored temperature (21±1° C.) and relative hygrometry (45±5%). Before the picture acquisitions, the hair strands were combed 5 times. They were placed in a clip with a black background. To ensure a good reproducibility of the acquisition conditions, the clip was fixed on an optical measurement bench specially developed by Spincontrol "Visio-Face®".

For each hair strand, the acquisition of non-cross polarized photographs was carried out before and after shampoo application. The photographs were transformed into cartographies of saturation (axis "S" in the colorimetric space HSL), which enabled to emphasize the contrast of the photographs in term of shininess. The cartographies of saturation obtained were coded in grey levels from 0 to 255. The intensity of the grey levels was calculated for each cartography of saturation. This parameter is directly correlated to the shininess of the hair. The intensity is expressed without any units.

The results of the shininess study are compiled in the following table:

| Shampoo | Hair Shininess (mean ± standard deviation) | | |
|---|---|---|---|
| | Before Treatment | After Treatment | Evolution of Hair Shininess |
| A | 96.9 ± 3.3 | 103.3 ± 3.0 | +6.6% |
| B | 94.9 ± 4.2 | 104.0 ± 3.7 | +9.6% |
| C | 95.0 ± 4.3 | 104.5 ± 2.6 | +9.6% |

The results were analysed according to the Student t test for paired groups at 5%, after the checking the normality of the distributions by Shapiro-Wilk test at 1%. A significant difference in evolution of hair shininess was found for the shampoos containing the hyaluronic acid mixture of the present invention (i.e. shampoos B and C) in comparison to the placebo shampoo A.

Brittleness

To assess brittleness, a special device was developed for treatment of the hair strands. This device is equipped with two vent brushes that are attached to a cylindrical mixing blade. The number of rotations and speed (rotation per minutes: rpm) are adjustable. For the present study, the device was set to 75 rpm. Simultaneously, the hair was subjected to hot air from a blow dryer, which was placed such that the hair was kept against the brushes during rotation.

The hair strands were treated for one hour, corresponding to approximately 9000 brush strokes. After the treatment, each hair strand was divided in three parts and separately combed five times. After each combing, brittle hair was collected and counted.

The results of the brittleness study are compiled in the following table:

| Shampoo | Number of Brittle Hair (mean ± standard deviation) | Improvement Compared to Placebo |
|---|---|---|
| A | 98 ± 63 | — |
| B | 34 ± 34 | −65% |
| C | 34 ± 23 | −65% |

The results were analysed according to the Mann-Whitney test at 5%, after the checking of the normality of the distribution by Shapiro-Wilk at 1%, and the checking of the homogeneity of the variances by the Fisher test at 5%. The statistical analysis shows a significant difference in the number of brittle hair between groups of hair strands treated with the shampoos of the present invention (i.e. shampoos B and C) in comparison to placebo group.

Microscopic Studies

After applying the rotation-brushing and heating treatment as described above for the brittleness study, the hair surface was also studied by Scanning Electron Microscopy (SEM), providing high resolution images. This analysis was carried out using a scanning electron microscope from ZEISS DSM 982 GEMINI—Probe EDS NORAN.

The hair strands were investigated (a) after shampooing and before treatment and (b) after shampooing and after treatment.

Figure 4A:
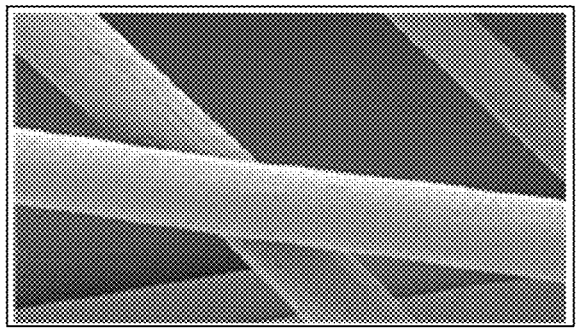
FIGS. 4a and 4b shows scanning electron microscopy (SEM) images (a) after shampooing and before rotation-brushing and heating treatment and (b) after shampooing and after rotation-brushing and heating treatment of hair strands treated with placebo shampoo.
Figure 4B:
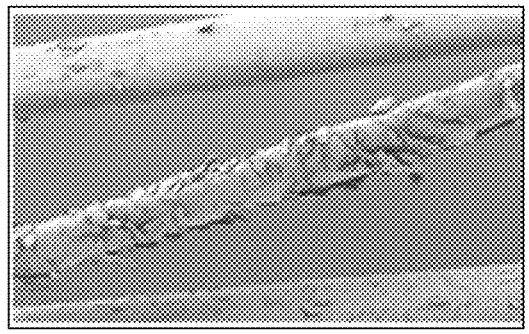
Figure 5A:
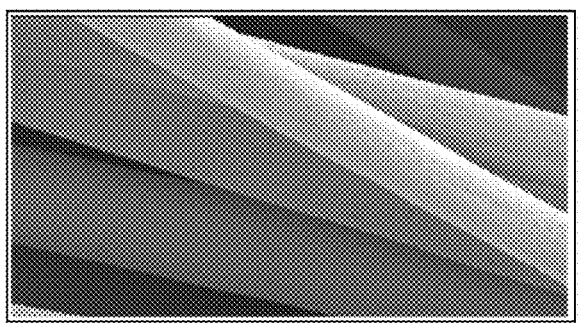
FIGS. 5a and 5b show scanning electron microscopy (SEM) images (a) after shampooing and before rotation-brushing and heating treatment and (b) after shampooing and after rotation-brushing and heating treatment of hair strands treated with shampoos according to the invention.
Figure 5B:
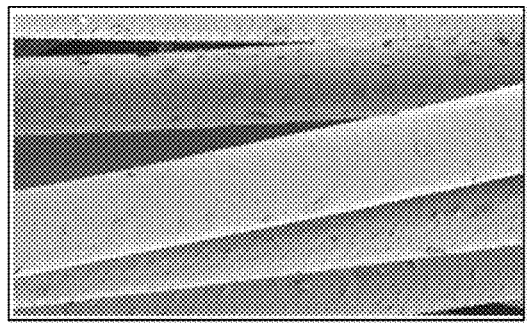
Figure 6A:
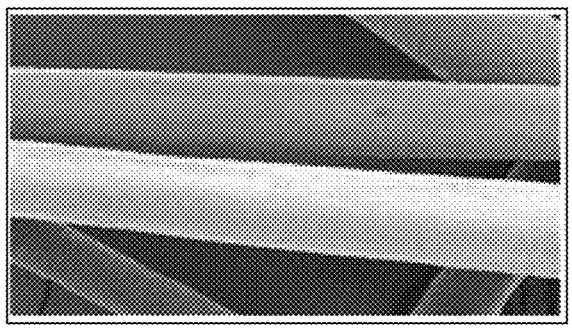
FIGS. 6a and 6b illustrate scanning electron microscopy (SEM) images (a) after shampooing and before rotation-brushing and heating treatment and (b) after shampooing and after rotation-brushing and heating treatment of hair strands treated with shampoos according to the invention.
Figure 6B:
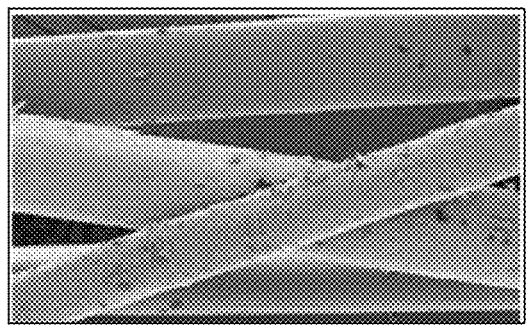

The results of the microscopic studies are shown in the following six figures:

| Shampoo | Before Treatment | After Treatment |
|---|---|---|
| A | FIG. 4a | FIG. 4b |
| B | FIG. 5a | FIG. 5b |
| C | FIG. 6a | FIG. 6b |

These figures illustrate the alteration of hair fibre materialized by the lifting of cuticles, which is the most relevant parameter to consider. The microscopic images show that the treatment with the above described combing device alters the hair and provokes the lifting of the cuticle. This effect is much more pronounced for placebo shampoo A in comparison to the shampoos of the present invention (i.e. shampoos B and C), where essentially no cuticle lifting was observed.

EXAMPLE 6: HYDRATION STUDY

For this study, commercially available straight, natural brown hair strands of human origin were used. The length of the hair strands was 15 cm.

The hair was divided in 15 strands of 10 g each and washed separately using a neutral shampoo. After the washing procedure, the strands were slightly bumped with a towel and then dried with a hairdryer. Subsequently, the hair strands were treated with the shampoos to be tested by applying 2 ml of shampoo to the wet hair strands, rubbing during 20 s, and rinsing during 30 s. After shampoo application, the hair strands were dried with a hairdryer.

Hair moisture content was measured indirectly using a Tewameter TM 300 (Courage+Khazaka, electronic GmbH), measuring the density gradient of the water evaporation. Water loss from the hair was continuously measured during one hour. For quantitative assessment, a calibration curve was prepared with known amounts of water (0, 10, 50, 100, 200, 400, and 600 µl).

Under the experimental conditions tested, shampoos B and C both increased the hair water content when compared to the placebo shampoo C. The hair water contents are compiled in the following table:

| Shampoo | Water Content (mean ± standard deviation) |
|---|---|
| A | 0.056 ± 0.01 |
| B | 1.47 ± 0.31 |
| C | 10.567 ± 1.18 |

Thus, the water content correlates with the concentration of the hyaluronic acid present in the shampoo.

EXAMPLE 7: ANTI-FRIZZ STUDY

The study was done on hair strands with different curly level. 10 hair strands per condition were tested.

At t0, 10 hair strands with different curl degree (from wavy to curly) were selected. Each hair strand was divided in equal parts (2 treated parts and one non-treated part) in order to have an equal distribution in terms of curl degree. Photographs were taken before washing.

The hair strands were washed with water (comparative example), or with one of shampoos A through G (see example 2 above. All hair strands were dried in open air. Photographs were taken after washing and drying.

The hair strands were then smoothed with a hair straightener. Photographs were taken immediately after hair smoothing.

Then, the hair strands were put in a room under extreme conditions of humidity (Relative humidity 80%±10% RH). Photographs of hair strands were taken after 4 hours (T4 h) and 8 hours (T8 h) in extreme conditions.

The photographs were analyzed using Photoshop® to study anti-frizz effect by the measure of hair strands length before and after four and eight hours in extreme conditions of humidity. The digital camera used was of type Nikon D7100. The photographs of hair strands were taken in standardized, indirect light. Aperture, speed and distance of the camera were also standardized. At each time point, the length of the hair strands was determined using Photoshop®.

FIG. 7 shows examples of photographs taken for treatments with water and shampoos A, B and C, according to the following arrangement:

From top to bottom, the four rows show hair strands treated with shampoo C; with shampoo B; with placebo shampoo A; and with water, respectively.

From left to right, the five columns show the hair strands before treatment (t0); after shampoo treatment; after smoothing with a hair straightener; after 4 hours in extreme humidity condition (t4 h); and after 8 hours in extreme humidity condition (t8 h), respectively.

FIG. 8 shows examples of photographs taken for treatments with shampoos A, C, D, and E, according to the following arrangement:

From top to bottom, the four rows show hair strands treated with shampoo D; with shampoo E; with placebo shampoo A; and with shampoo C, respectively.

From left to right, the five columns show the hair strands before treatment (t0); after shampoo treatment; after smoothing with a hair straightener; after 4 hours in extreme humidity condition (t4 h); and after 8 hours in extreme humidity condition (t8 h), respectively.

FIG. 9 shows examples of photographs taken for treatments with shampoos A, C, F, and G, according to the following arrangement:

From top to bottom, the four rows show hair strands treated with shampoo F; with shampoo G; with placebo shampoo A; and with shampoo C, respectively.

From left to right, the five columns show the hair strands before treatment (t0); after shampoo treatment; after smoothing with a hair straightener; after 4 hours in extreme humidity condition (t4 h); and after 8 hours in extreme humidity condition (t8 h), respectively.

The length of each hair strand at t4 h and t8 h was compared to that directly after smoothing to determine a smoothing percentage. The results are shown in the following table:

|  | Smoothing Percentage (mean ± standard deviation) | |
| --- | --- | --- |
|  | t4 h | t8 h |
| Water | 71 ± 3% | 69 ± 3% |
| Shampoo A | 88 ± 4% | 83 ± 4% |
| Shampoo B | 94 ± 3% | 87 ± 2% |
| Shampoo C | 97 ± 1% | 94 ± 2% |
| Shampoo D | 58 ± 6% | 55 ± 6% |
| Shampoo E | 58 ± 7% | 52 ± 10% |
| Shampoo F | 70 ± 5% | 64 ± 10% |
| Shampoo G | 63 ± 2% | 57 ± 4% |

Thus, both after 4 hours and 8 hours in extreme condition of humidity, the hair strands treated with shampoos B and C showed significantly greater length and thus greater smoothness than the hair strands treated with shampoo A or water, whereas shampoos D, E, F, and G proved worse.

EXAMPLE 8: ASSESSMENT OF INFLUENCE OF SHAMPOO ON HAIR BEAUTY IN NORMAL LIFE CONDITIONS

This study enrolled Caucasian women (age 18 and older) having damaged hair such as dull, dry, lack of volume. The study was a double blind and parallel groups study. 23 volunteers received shampoo A (comparative example), while shampoos B and C were provided to 24 volunteers each. All of the subjects participating in the study gave their informed consent signed at the beginning of the study.

Volunteers applied the shampoo twice a week on their scalp and hair. They applied a small amount of the product on wet hair, then after a massage of the entire scalp and hair, they rinsed the product with water. On Days 0, 14 and 28, a hair-dresser assessed the softness, shininess, and volume of the hair using a scale. In addition, subjects were asked to answer to a subjective questionnaire related to product properties, their global efficacy and their future use on day 28.

At each visit (DO, D14 and D28), the hairdresser assessed the overall hair beauty and hair appearance using 3 different beauty parameters, each one assessed by means of a 10-points-scale:

For shininess, a value close to 1 means dull hair and a value close to 10 means shiny hair.

For softness, a value close to 1 means rough and stiff hair, whereas a value close to 10 means soft, elastic and supple hair.

For volume, a value close to 1 means lack of volume and a value close to 10 means lots of volume.

It was found that hair aspect was visibly improved after 14 and 28 days of use for all three products.

However, shampoos B and C lead to a stronger increase in volume and larger improvement of softness than the placebo shampoo A.

The results of the questionnaire are compiled in the following table:

|  | Shampoo A | Shampoo B | Shampoo C |
| --- | --- | --- | --- |
| Hair easy to disentangle | 74% | 71% | 75% |
| Hair easy to comb | 78% | 84% | 88% |
| Light hair | 78% | 96% | 96% |
| Voluminous hair | 68% | 59% | 91% |
| Resistant hair, strong | 60% | 79% | 79% |
| Revitalized hair | 59% | 79% | 79% |
| Product adds body and matter to hair | 65% | 71% | 79% |
| Smooth hair | 60% | 62% | 71% |
| Soft hair | 82% | 92% | 96% |
| Supple hair | 82% | 96% | 87% |
| Shiny hair | 73% | 88% | 92% |
| More satisfaction than usual product | 48% | 63% | 63% |
| Would like to continue to use the product | 65% | 75% | 96% |
| Might buy this product (regardless of price) at the end of this study | 61% | 71% | 88% |

EXAMPLE 9: ASSESSMENT OF INFLUENCE OF SHAMPOO ON HAIR BEAUTY IN HAMMAM CONDITIONS

This study enrolled 9 Caucasian women (age 18 and older) having the habit to smooth their hair with a hair straightener. The study was a simple blind study. All volunteers tested both placebo shampoo A and shampoo C. All of the subjects participating to the study gave their informed consent.

Volunteers washed their hair in the clinical centre with the respective shampoo, rinsed it with water, dried, and smoothed their hair. The volunteers then underwent a hamman session in a room at 43° C. and 100% RH for 20 minutes.

The study was realized on one day with each product tested. Photographs of the hair were taken at different times:
 T0: after washing their hair with the respective shampoo on wet hair
 T1: after hair smoothing and before hamman session
 T2: immediately after hamman session Based on the photographs, it was found that shampoo C improved hair beauty by providing more volume and a homogenous aspect to the hair, whereas shampoo A left the hair with an entangled aspect.

EXAMPLE 10: ASSESSMENT OF INFLUENCE OF HAIR SPRAY ON HAIR BEAUTY IN HAMMAM CONDITIONS

This study enrolled 8 Caucasian women (age 18 and older) having the habit to smooth their hair with a hair straightener. The study was a simple blind study. All volunteers tested both spray A and spray B (see example 3 above). All of the subjects participating to the study gave their informed consent.

Volunteers washed their hair in the clinical centre, applying their usual shampoo on their scalp and hair. After rinsing their hair, a technician sprayed the respective hair spray on the wet hair. After that, the hair was dried and smoothed. The volunteers underwent a hamman session in a room at 43° C. and 100% RH for at least 30 minutes.

The study was realized on one day with each product tested. Photographs of the hair were taken at different times:

T0: after their usual shampoo on wet hair and before product spraying

T1: after product spraying and before hair drying and smoothing

T2: after hair smoothing and before Hamman session

T3: immediately after hamman session

Based on the photographs, it was found that spray B improves hair beauty by providing more volume to the hair and a homogenous aspect, whereas spray A left the hair with an entangled and flat aspect.

The invention claimed is:

1. A hair care composition effective in reducing hair frizz after application to hair, comprising a low molecular weight hyaluronic acid fraction and a high molecular weight hyaluronic acid fraction, wherein the low molecular weight hyaluronic acid fraction comprises hyaluronic acid or a salt or derivative thereof having a weight-average molecular weight $M_w$ of 20 to 50 kDa and the high molecular weight hyaluronic acid fraction comprises hyaluronic acid or a salt or derivative thereof having a weight-average molecular weight $M_w$ of 1 to 20 MDa, wherein the composition includes no hyaluronic acid or a salt or derivative thereof of intermediate molecular weight, having a weight-average molecular weight $M_w$ of more than 50 kDa to less than 1 MDa, wherein the composition further comprises a cationic conditioner that is hydroxypropyl guar hydroxypropyl trimonium chloride.

2. The hair care composition of claim 1, comprising at least 0.1% by weight of the low molecular weight hyaluronic acid fraction.

3. The hair care composition of claim 1, comprising at least 0.1% by weight of the high molecular weight hyaluronic acid fraction.

4. The hair care composition of claim 1, wherein the weight ratio of the low molecular weight hyaluronic acid fraction to the high molecular weight hyaluronic acid fraction is 1:1 to 10:1.

5. The hair care composition of claim 1, comprising about 2 wt. % to 5 wt. % of a hyaluronic acid mixture; up to about 2 wt. % of 80 wt. % lactic acid; up to about 3 wt. % of phenoxyethanol; wherein the hyaluronic acid mixture comprises about 0.2 wt. % to 2 wt. % of high molecular weight hyaluronic acid and about 1 wt. % to about 3 wt. % of low molecular weight hyaluronic acid, based on the total weight of the composition.

6. A consumer hair care product, comprising the hair care composition according to claim 1.

7. The consumer hair care product of claim 6, comprising at least 1% by weight of the hair care composition of claim 1.

8. The consumer hair care product of claim 6, selected from the group consisting of:

shampoo, conditioner, spray, treatment, mask, strengthener, pre-shampoo, lotion, serum, cream, foam, mousse, and gel.

9. The consumer hair care product of claim 6, further comprising one or more materials selected from the group consisting of:

carriers, solvents, surfactants, thickeners, styling polymers, anti-dandruff actives, antimicrobial materials, skin and scalp actives, vitamins, salts, buffers, hair growth agents, conditioning materials, hair-fixative polymers, fragrances, colorings/colorants, dyes, pigments, opacifiers, pearlescent aids, oils, waxes, preservatives, sensates, sunscreens, medicinal agents, antifoaming agents, antioxidants, binders, biological additives, buffering agents, bulking agents, chelating agents, chemical additives, film formers or materials, pH adjusters, propellants, oxidizing agents, and reducing agents.

10. A method of reducing hair frizz, the method comprising the step of: applying to the hair an effective amount of the hair care composition of claim 1.

11. The hair care composition of claim 1, wherein the high molecular weight hyaluronic acid fraction comprises hyaluronic acid or a salt or derivative thereof having a weight-average molecular weight $M_w$ of 1 to 5 MDa.

12. The hair care composition of claim 2, comprising 1% to 10% by weight of the low molecular weight hyaluronic acid fraction.

13. The hair care composition of claim 3, comprising 0.1% to 5% by weight of the high molecular weight hyaluronic acid fraction.

14. The hair care composition of claim 4, wherein the weight ratio of the low molecular weight hyaluronic acid fraction to the high molecular weight hyaluronic acid fraction is 2:1 to 6:1.

15. The hair care composition of claim 1, comprising about 0.01% to about 0.5% by weight of hydroxypropyl guar hydroxypropyl trimonium chloride.

* * * * *